US012377029B2

(12) United States Patent
Sudo et al.

(10) Patent No.: US 12,377,029 B2
(45) Date of Patent: *Aug. 5, 2025

(54) ALCOHOL COMPOSITION

(71) Applicant: SHIN-ETSU CHEMICAL CO., LTD., Tokyo (JP)

(72) Inventors: Takane Sudo, Joetsu (JP); Shingo Niinobe, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 86 days.

This patent is subject to a terminal disclaimer.

(21) Appl. No.: 17/467,272

(22) Filed: Sep. 6, 2021

(65) Prior Publication Data

US 2022/0071869 A1   Mar. 10, 2022

(30) Foreign Application Priority Data

Sep. 8, 2020   (JP) .................................. 2020-150857

(51) Int. Cl.
*A61K 8/34* (2006.01)
*A01N 25/02* (2006.01)
*A01N 25/10* (2006.01)
*A01N 31/02* (2006.01)
*A01N 43/16* (2006.01)
*A01P 1/00* (2006.01)
*A61K 8/73* (2006.01)
*A61K 9/00* (2006.01)
*A61K 31/045* (2006.01)
*A61K 47/38* (2006.01)
*A61P 17/00* (2006.01)
*A61P 31/02* (2006.01)
*A61Q 17/00* (2006.01)
*A61Q 19/00* (2006.01)

(52) U.S. Cl.
CPC ..................................... *A61K 8/34* (2013.01); *A01P 1/00* (2021.08); *A61K 8/731* (2013.01); *A61K 9/0014* (2013.01); *A61K 31/045* (2013.01); *A61K 47/38* (2013.01); *A61P 17/00* (2018.01); *A61P 31/02* (2018.01); *A61Q 17/005* (2013.01); *A61Q 19/00* (2013.01); *A61K 2800/30* (2013.01); *A61K 2800/48* (2013.01)

(58) Field of Classification Search
None
See application file for complete search history.

(56) References Cited

U.S. PATENT DOCUMENTS

| | | |
|---|---|---|
| 5,750,579 A | 5/1998 | Kamishita |
| 2007/0065388 A1 | 3/2007 | Miyamoto |
| 2008/0262216 A1 | 10/2008 | Hayakawa |
| 2022/0071871 A1 | 3/2022 | Sudo |

FOREIGN PATENT DOCUMENTS

| | | |
|---|---|---|
| CN | 101953779 | 1/2011 |
| EP | 0 604 848 | 7/1994 |
| EP | 3747962 | 12/2020 |
| JP | H-11209230 | 8/1999 |
| JP | 2005132782 | 5/2005 |
| JP | 2007084479 | 4/2007 |
| JP | 2010006978 | 1/2010 |
| JP | 2011-173823 | 9/2011 |
| JP | 2016183313 | 10/2016 |
| JP | 2016188254 | 11/2016 |
| JP | 2018-012663 | 1/2018 |
| JP | 2020019746 | 2/2020 |
| TW | I415860 B * | 2/2009 |
| WO | 2006-085907 | 8/2006 |

OTHER PUBLICATIONS

TWI415860B—Goggle English Translation (Year: 2009).*
HPMC (ChemBK), ([obtained from on-line website: https://www.chembk.com/en/chem/HPMC, last visit Jan. 19, 2024]) (Year: 2024).*
Extended European Search Report of corresponding EP patent application; Patent Application No. EP 21195223.9; Date of Drafting: Feb. 9, 2022.
"Hydroxypropylcellulose," in the Japanese Pharmacopoeia, eighteenth edition, 2021, available at https://www.pmda.go.jp/english/rs-sb-std/standards-development/jp/0029.html.
"Hypromellose" in the Japanese Pharmacopoeia, eighteenth edition, 2021, available at https://www.pmda.go.jp/english/rs-sb-std/standards-development/jp/0029.html.
Office Action from JPO (English machine translation of Office Action), Patent Application No. JP2020-150857, Date of Drafting: Oct. 24, 2023.
Office Action from JPO (English machine translation of Office Action), Patent Application No. JP2020-150857 Date of Drafting: Jun. 30, 2023.

(Continued)

*Primary Examiner* — Kyung S Chang
(74) *Attorney, Agent, or Firm* — JMB Davis Ben-David

(57) ABSTRACT

It is an objective of the present invention to provide an alcohol composition in which hydroxypropyl methylcellulose or methylcellulose is contained in such a way that its thickening ability is exhibited so that the alcohol composition can have a viscosity that is easy to apply and difficult to spill down, and can be prevented from dripping out and/or can have high transparency, and further can have a good application feeling. The objective can be achieved by an alcohol composition comprising 60.0 parts by mass to 93.0 parts by mass of at least one alcohol selected from the group consisting of ethanol and isopropanol, 3.0 parts by mass to 39.9 parts by mass of water, and 0.1 parts by mass to 4.0 parts by mass of at least one water-soluble cellulose ether selected from the group consisting of hydroxypropyl methylcellulose and methylcellulose, wherein the alcohol composition has a loss tangent (tan δ) of 0.10 to 1.00 when measured at 20° C. under the condition of being a frequency of 1 Hz and a strain of 0.1%, and so on.

6 Claims, No Drawings

(56) References Cited

OTHER PUBLICATIONS

Office Action from JPO (English machine translation of Office Action) Patent Application No. JP2020-150857 Date of Drafting: May 7, 2024.
Extract from European Pharmacopoeia 11.0 on HPMC, pp. 3055-3057.
European Patent Office, EPO Communication pursuant to Article 94(3) of corresponding EP Patent Application No. 21195223.9, Date of Issuance: Dec. 17, 2024, pp. 1-4, Germany.
China National Intellectual Property Administration, Office Action issued in Chinese Patent Application No. 202111044765.1, Date of Issuance: May 17, 2025, pp. 1-7.
Taiwan Intellectual Property Office, Office Action issued in Taiwanese Patent Application No. 110133391, Date of Issuance: Apr. 9, 2025, pp. 1-7.

\* cited by examiner

ALCOHOL COMPOSITION

CROSS-REFERENCE TO RELATED APPLICATION

The present application claims the benefit of priority to Japanese Patent Application No. 2020-150857, filed on Sep. 8, 2020, the contents of which are incorporated by reference herein in their entirety.

TECHNICAL FIELD

The present invention relates to alcohol compositions.

BACKGROUND ART

Alcohol compositions are widely used in industrial and domestic applications. Examples of such applications include hand sanitizers containing mono alcohols and water; and those containing polyhydric alcohols including pharmaceutical and food coolants, cosmetics such as hair gel, and aromatics. In this way, the alcohol compositions are used in various applications.

In particular, the demand for alcohol hand sanitizers increased dramatically in the year of 2020, and the alcohol hand sanitizers are widely used not only in medical and nursing cares, but also in households. For example, a highly viscous gel hand sanitizer has the advantages of being difficult to spill down from hands and being easy to carry around. In order to produce such a gel hand sanitizer, viscosity adjustment is required.

Thickening agents are used to adjust the viscosity of the alcohol composition, and examples of such thickening agents include acrylic polymers, polyvinyl alcohols, xanthan gum, and cellulose derivatives. For example, alcohol compositions may contain acrylic polymers, xanthan gum and cellulose derivatives as thickening agents (see Patent Document 1).

CITATION LIST

Patent Documents

Patent Document 1: JP 2008-508189 A

SUMMARY OF THE INVENTION

Problems to be Solved by the Invention

However, the alcohol composition described in Patent Document 1 has the problem of containing the thickening agents in the amount as little as 0.3%. In addition to this, cellulose ethers such as hydroxypropyl methylcellulose (hereinafter also referred to as "HPMC") and methylcellulose (hereinafter also referred to as "MC") have low solubility in alcohols. Therefore, when such cellulose ethers are added to a composition for hand sanitizer with a high alcohol concentration, the composition may contain such cellulose ethers in the undissolved state so that thickening is not achieved, and the composition can have problems of dripping out when dispensed and being low transparency.

Furthermore, commonly used acrylic polymers give the resulting alcohol composition a light application feeling, thereby tending to cause a feeling of dryness after application.

In addition to these circumstances, in recent years, there has been a growing social awareness of the need to use sustainable resources with less environmental impact. Sustainable resource components including cellulose ethers such as hydroxypropyl methylcellulose and methylcellulose are preferred as replacements of synthetic polymers from an environmental perspective.

In view of the above circumstances, it is an objective of the present invention to provide an alcohol composition in which hydroxypropyl methylcellulose or methylcellulose is contained for its thickening ability, characterized by a viscosity associated with ease of application, limited spillage from hands or containers, high transparency, and/or a good application feeling.

Means of Solving the Problems

In the course of extensive efforts to find a way to solve the above-identified problems, the present inventors have succeeded in producing an alcohol composition containing hydroxypropyl methylcellulose or methylcellulose in the dissolved state in which its thickening ability is exhibited even when the alcohol concentration is high. Surprisingly, it has been found out that the resulting alcohol composition has a viscosity that is easy to apply and difficult to spill down as well as preventing dripping, and further has a good application feeling lacking stickiness; the resulting alcohol composition has a viscosity that is easy to apply and difficult to spill down, as well as has high transparency, and further has a moist application feeling; or the resulting alcohol composition has a viscosity that is easy to apply and difficult to spill down, prevents dripping, has high transparency, and further has good application feeling lacking stickiness. Finally, based on the above findings, the present inventors have succeeded in inventing alcohol compositions containing hydroxypropyl methylcellulose or methylcellulose in the dissolved state in which its thickening ability is exhibited so that the alcohol composition can have various excellent properties. As such, the present invention has been completed on the basis of the findings and successful examples that were first found or obtained by the present inventors.

According to the present invention, there is provided each alcohol composition in the following aspects:

A first aspect of the present invention is an alcohol composition containing 60.0 parts by mass to 93.0 parts by mass of at least one alcohol selected from the group consisting of ethanol and isopropanol, 3.0 parts by mass to 39.9 parts by mass of water, and 0.1 parts by mass to 4.0 parts by mass of at least one water-soluble cellulose ether selected from the group consisting of hydroxypropyl methylcellulose and methylcellulose, wherein the alcohol composition has a viscoelasticity characterized by a loss tangent (tan δ) of 0.10 to 1.00 when measured at 20° C. under the condition of being a frequency of 1 Hz and a strain of 0.1%.

The alcohol composition according to the first aspect of the present invention preferably has a viscosity equal to or more than 2,500 mPa·s when measured with a viscometer at 20° C. using a 2.0% by mass aqueous solution.

The alcohol composition according to the first aspect of the present invention preferably does not contain at least one additive selected from the group consisting of hydroxyethyl cellulose and carboxyvinyl polymer.

A second aspect of the present invention is an alcohol composition containing 40.0 parts by mass to 88.0 parts by mass of at least one alcohol selected from the group consisting of ethanol and isopropanol, 8.0 parts by mass to 59.9 parts by mass of water, and 0.1 parts by mass to 4.0 parts by mass of at least one water-soluble cellulose ether selected from the group consisting of hydroxypropylmethylcellulose and methylcellulose, wherein the alcohol composition has a transmittance equal to or more than 65.0%.

The alcohol composition according to the second aspect of the present invention preferably has a viscosity equal to or more than 1,500 mPa·s when measured with a viscometer at 20° C. using a 2.0% by mass aqueous solution.

The alcohol composition according to the second aspect of the present invention preferably does not contain at least one additive selected from the group consisting of hydroxyethyl cellulose and carboxyvinyl polymer.

A third aspect of the present invention is an alcohol composition containing 60.0 parts by mass to 88.0 parts by mass of at least one alcohol selected from the group consisting of ethanol and isopropanol, 8.0 parts by mass to 39.9 parts by mass of water, and 0.1 parts by mass to 4.0 parts by mass of at least one water-soluble cellulose ether selected from the group consisting of hydroxypropyl methylcellulose and methylcellulose, wherein the alcohol composition has a loss tangent (tan δ) of 0.10 to 1.00 when measured at 20° C. under the condition of being a frequency of 1 Hz and a strain of 0.1%, and has a transmittance equal to or more than 65.0%.

The alcohol composition according to the third aspect of the present invention preferably has a viscosity equal to or more than 2,500 mPa·s when measured with a viscometer at 20° C. using a 2.0% by mass aqueous solution.

The alcohol composition according to the third aspect of the present invention preferably does not contain at least one additive selected from the group consisting of hydroxyethyl cellulose and carboxyvinyl polymer.

Effect of the Invention

According to the alcohol composition of the first embodiment of the present invention, even if the alcohol concentration is relatively high, the water-soluble cellulose ether added as a thickening agent is sufficiently dissolved to produce an alcohol composition which has a viscosity that is easy to apply and difficult to spill down, does not drip out, and has pleasant rather than sticky application feeling.

According to the alcohol composition of the second embodiment of the present invention, even if the alcohol concentration is relatively high, the water-soluble cellulose ether added as a thickening agent is sufficiently dissolved to produce an alcohol composition which has a viscosity that is easy to apply and difficult to spill down, has attractive high transparency, retains stable viscosity stability, and has a moist application feeling.

According to the alcohol composition of the third embodiment of the present invention, even if the alcohol concentration is relatively high, the water-soluble cellulose ether added as a thickening agent is sufficiently dissolved to produce an alcohol composition which has a viscosity that is easy to apply and difficult to spill down, does not drip out, has attractive high transparency, retains stable viscosity, and has a pleasant rather than sticky application feeling.

Each embodiment of the present invention provides an alcohol composition with the above properties even if the alcohol concentration is equal to or more than 60% by mass.

DETAILED DESCRIPTION OF EMBODIMENTS

While each alcohol composition that forms one embodiment of the present invention will now be described in detail, the present invention may take various forms to the extent that its objective can be achieved.

Unless otherwise specified, each term used herein is used in the meaning commonly used by those skilled in the art, and should not be construed to have any meaning that is unduly limiting. Also, any speculations and theories herein are made on the basis of the knowledge and experiences of the present inventors and as such, the present invention is not bound by any such speculations and theories.

While the term "composition" is not particularly limited and means any composition as well known, it is, for example, comprised of combination of two or more components.

The term "and/or" as used herein means either any one of, any combination of two or more of, or combination of all of listed related items.

The term "content" as used herein is almost equivalent to "concentration" and "amount used" ("amount added"), and means the proportion of the amount of a component relative to the total amount of a composition containing the component. Unless otherwise specified, the unit of content herein indicates parts by mass. It should be noted, however, that the total amount of the contents of components do not exceed 100 parts by mass.

The wording "to" for indicating a range of values is intended to include both values preceding and following the wording; for example, "0% to 100%" means a range from 0% or more and 100% or less. The terms "more than" and "less than" used herein means the lower and upper limits without including a value following the term, respectively. For example, "more than 1" means a value beyond 1, and "less than 100" means a value below 100.

The terms "include," "comprise," and "contain" mean that an element(s) other than an element(s) as explicitly indicated can be added as inclusions, which are, for example, synonymous with "at least include," but encompasses the meaning of "consist of" and "substantially consist of". In other words, the terms may mean, for example, to include an element(s) as explicitly indicated as well as any one element or any two or more elements, to consist of an element(s) as explicitly indicated, or substantially consist of an element(s) as explicitly indicated. Such elements include limitations such as components, steps, conditions, and parameters.

The number of digits of an integer equals to its significant figure. For example, 1 has one significant figure and 10 has two significant figures. For a decimal number, the number of digits after a decimal point equals to its significant figure. For example, 0.1 has one significant figure and 0.10 has two significant figures.

The alcohol composition according to one embodiment of the present invention contains at least one alcohol selected from the group consisting of ethanol and isopropanol, water, and at least one water-soluble cellulose ether selected from the group consisting of hydroxypropyl methylcellulose and methylcellulose; and has a viscosity that is easy to apply and difficult to spill down.

The alcohol composition according to each embodiment of the present invention has differences in the above-mentioned contents of alcohol, water and water-soluble cellulose ether, and thus has differences in properties from each other. The alcohol composition according to each embodiment of the present invention can be classified into three general groups. The alcohol composition according to the first embodiment of the present invention is also referred to herein as "alcohol composition A", the alcohol composition according to the second embodiment of the present invention as "alcohol composition B", and the alcohol composition according to the third embodiment of the present invention as "alcohol composition C", respectively.

That is, alcohol composition A contains 60.0 part by mass to 93.0 parts by mass of at least one alcohol selected from the group consisting of ethanol and isopropanol, 3.0 parts by mass to 39.9 parts by mass of water, and 0.1 parts by mass to 4.0 parts by mass of at least one water-soluble cellulose ether selected from the group consisting of hydroxypropyl methylcellulose and methylcellulose. Alcohol composition A is characterized by having a loss tangent (tan δ) of 0.10 to 1.00 when measured at 20° C. under the condition of being a frequency of 1 Hz and a strain of 0.1%. Alcohol composition A exerts advantageous effects of being prevented from dripping out, and further having no sticky feeling but a good application feeling.

Alcohol composition B contains 40.0 parts by mass to 88.0 parts by mass of at least one alcohol selected from the group consisting of ethanol and isopropanol, 8.0 parts by mass to 59.9 parts by mass of water, and 0.1 parts by mass to 4.0 parts by mass of at least one water-soluble cellulose ether selected from the group consisting of HPMC and MC. Alcohol composition B is characterized by having a transmittance equal to or more than 65.0%. Alcohol composition B exerts advantageous effects of having high transparency and having a moist application feeling.

Alcohol composition C contains 60.0 parts by mass to 88.0 parts by mass of at least one alcohol selected from the group consisting of ethanol and isopropanol, 8.0 parts by mass to 39.9 parts by mass of water, and 0.1 parts by mass to 4.0 parts by mass of at least one water-soluble cellulose ether selected from the group consisting of HPMC and MC. Alcohol composition C is characterized by having a loss tangent (tan δ) of 0.10 to 1.00 when measured at 20° C. under the condition of being a frequency of 1 Hz and a strain of 0.1%, and a transmittance equal to or more than 65.0%. Alcohol composition C exerts advantageous effects of having a viscosity that is easy to apply and difficult to spill down, capable of being prevented from dripping out, having high transparency, and further having no sticky feeling but a good application feeling.

While alcohol composition A, alcohol composition B, and alcohol composition C will be described in detail below, common features may be referred to each other.

<Alcohol Composition A>

In order to increase the viscosity of alcohol composition with the use of a viscosity conditioning agent, it is preferable that such a viscosity conditioning agent be homogeneously dissolved in the entire alcohol composition. When water-soluble cellulose ethers such as HPMC and MC, which are difficult to dissolve in alcohols, are used as the viscosity conditioning agents, the conventional method to dissolve HPMC and MC is to increase the ratio of water, therefore lowering the alcohol concentration.

However, the present inventors have found that even if the alcohol concentration is relatively high, an alcohol composition, which contains water-soluble cellulose ethers in the dissolved state such that each thickening ability is exhibited and further has a loss tangent (tan δ) of 0.10 to 1.00 when measured at 20° C. under the condition of being a frequency of 1 Hz and a strain of 0.1%, has excellent viscoelasticity. By achieving such characteristic rheology, alcohol composition A can be prevented from dripping out and has no sticky feeling but a good application feeling, in addition to having a viscosity that is easy to apply and difficult to spill down, even with a high concentration of alcohol. As a result, alcohol composition A can even take, for example, the gel form with appropriate viscosity.

[Alcohol]

The alcohol used is ethanol, isopropanol, or a mixture of ethanol and isopropanol.

The content of alcohol in alcohol composition A is in the range between 60.0 parts by mass and 93.0 parts by mass. For example, from the viewpoint of the solubility of the water-soluble cellulose ether and the thickening property imparted by the water-soluble cellulose ether, the content is preferably in the range between 60.0 parts by mass and 90.0 parts by mass, and more preferably 63.0 parts by mass and 85.0 parts by mass. When the alcohol composition is employed as a disinfectant alcohol composition, it is preferable that the content of alcohol be 70.0 parts by mass or more.

[Water]

While water is not particularly limited, examples of water include ion exchange water, distilled water, and tap water. So long as the water-soluble cellulose ether can be dissolved, an aqueous solution prepared by adding salts, water-soluble polymers, or other components to water may be used.

The content of water in alcohol composition A is in the range between 3.0 parts by mass and 39.9 parts by mass. For example, from the viewpoint of the solubility of the water-soluble cellulose ether and the thickening property imparted by the water-soluble cellulose ether, the content is preferably in the range between 6.0 parts by mass and 39.9 parts by mass, and more preferably 11.0 parts by mass and 36.9 parts by mass.

[Hydroxypropyl Methylcellulose (HPMC)]

HPMC is a water-soluble cellulose ether formed by introducing methoxy and hydroxypropoxy groups into cellulose. HPMC according to the invention may have a range of physical properties, such as the methoxy group content (the degree of substitutions of methoxy groups), the hydroxypropoxy group content (the molar substitutions of hydroxypropoxy groups), the viscosity and the molecular weight. HPMC may be selected as appropriate according to the viscosity and other properties to be imparted to the resulting alcohol composition. While the method of obtaining HPMC is not particularly limited, HPMC may be produced by known production methods or obtained as commercially available products.

One example of the method of producing HPMC can include the steps of reacting cellulose pulp with alkali to obtain an alkali cellulose, reacting the obtained alkali cellulose with a hydroxypropyl etherifying agent and a methylating agent to obtain a reactant, and then washing, drying, and pulverizing the obtained reactant to prepare a water-soluble hydroxypropyl methylcellulose.

The viscosity of HPMC is not particularly limited. For example, in order to impart the desired viscosity to the alcohol composition, the viscosity when measured with a viscometer at 20° C. using a 2.0% by mass aqueous solution of HPMC is preferably in the range between 1,000 mPa·s and 120,000 mPa·s, more preferably 1,500 mPa·s and 100,000 mPa·s, and still more preferably 2,000 mP·s and 100,000 mPa·s. If the viscosity measured with a viscometer at 20° C. using a 2.0% by mass aqueous solution of HPMC is in the range between 1,000 mPa·s and 120,000 mPa·s, the resulting alcohol composition can have a viscosity at 20° C. which can take the gel form, liquid form, or other desired forms. Furthermore, if the viscosity when measured with a viscometer at 20° C. using a 2.0% by mass aqueous solution of HPMC is less than 1,000 mPa·s, the thickening property imparted to the alcohol composition may be too weak, and the viscosity stability of the alcohol composition may be insufficient. On the other hand, if the viscosity when measured with a viscometer at 20° C. using a 2.0% by mass aqueous solution of HPMC is more than 120,000 mPa·s, HPMC may become incompatible with alcohols, resulting in poor solubility and consequently poor thickening property and/or poor transparency of the alcohol composition. The viscosity of 2.0% by mass aqueous HPMC solution at 20° C. is measured using a single cylinder-type rotational viscometer according to "2. Method II Viscosity measurement by rotational viscometer" in the Viscosity Determination in General Tests described in Japanese Pharmacopoeia, 17th edition, as described in Examples below.

The degree of substitutions (DS) of methoxy groups in HPMC is preferably equal to or more than 1.00, more preferably in the range between 1.20 and 2.20, and still more preferably 1.30 and 2.10, from the viewpoint of compatibility with alcohols, dispersibility in alcohols, and viscoelasticity and transparency of the alcohol composition. The degree of substitutions (DS) of methoxy groups refers to the average number of methoxy groups per unit of anhydrous glucose.

The molar substitutions (MS) of hydroxypropoxy groups in HPMC is preferably equal to or more than 0.10, more preferably in the range between 0.10 and 0.60, and still more preferably 0.13 and 0.40, from the viewpoint of compatibility with alcohols, dispersibility in alcohols, and viscoelasticity and transparency of the alcohol composition. The molar substitutions (MS) of hydroxypropoxy groups in HPMC refers to the average number of moles of hydroxypropoxy groups per mole of anhydrous glucose.

DS of methoxy groups and MS of hydroxypropoxy groups in HPMC are determined by converting the values measured by the measurement method for Hypromellose (Hydroxypropyl Methylcellulose) described in Japanese Pharmacopoeia, 17th edition.

HPMC employed may vary depending on the alcohol concentration, and will be explained in detail in the section below explaining conditions for producing alcohol compositions A to C.

[Methylcellulose (MC)]

MC is a water-soluble cellulose ether formed by introducing methoxy groups into cellulose. MC according to the invention may have a range of physical properties, such as the methoxy group content (the degree of substitutions of methoxy groups), the viscosity and the molecular weight. MC may be selected as appropriate according to the viscosity and other properties to be imparted to the resulting alcohol composition. While the method of obtaining MC is not particularly limited, MC may be produced by known production methods or obtained as commercially available products.

One example of the method of producing MC can include the steps of reacting cellulose pulp with alkali to obtain an alkali cellulose, reacting the obtained alkali cellulose with a methylating agent to obtain a reactant, and then washing, drying, and pulverizing the obtained reactant to prepare a water-soluble methylcellulose.

The viscosity of MC is not particularly limited. For example, in order to impart the desired viscosity to the alcohol composition, the viscosity when measured with a viscometer at 20° C. using a 2.0% by mass aqueous solution of MC is preferably in the range between 1,000 mPa·s and 50,000 mPa·s, more preferably 1,500 mPa·s and 40,000 mPa·s, and still more preferably 2,000 mP·s and 30,000 mPa·s. If the viscosity measured with a viscometer at 20° C. using a 2.0% by mass aqueous solution of MC is in the range between 1,000 mPa·s and 50,000 mPa·s, the resulting alcohol composition can have a viscosity at 20° C. which can take the gel form, liquid form, or other desired forms. Furthermore, if the viscosity when measured with a viscometer at 20° C. using a 2.0% by mass aqueous solution of MC is less than 1,000 mPa·s, the thickening property imparted to the alcohol composition may be too weak, and the viscosity stability of the alcohol composition may be insufficient. On the other hand, if the viscosity when measured with a viscometer at 20° C. using a 2.0% by mass aqueous solution of MC is more than 50,000 mPa·s, MC may become incompatible with alcohols, resulting in poor solubility and consequently poor thickening property and/or poor transparency of the alcohol composition. The viscosity of 2.0% by mass aqueous MC solution at 20° C. is measured using a single cylinder-type rotational viscometer according to "2. Method II Viscosity measurement by rotational viscometer" in the Viscosity Determination in General Tests described in Japanese Pharmacopoeia, 17th edition, as described in Examples below.

The degree of substitutions (DS) of methoxy groups in MC is preferably in the range between 1.00 and 2.20, more preferably 1.30 and 2.10, and still more preferably 1.50 and 2.00, from the viewpoint of compatibility with alcohols, dispersibility in alcohols, and viscoelasticity and transparency of the alcohol composition. The degree of substitutions (DS) of methoxy groups refers to the average number of methoxy groups per unit of anhydrous glucose.

DS of methoxy groups in MC is determined by converting the value measured by the measurement method for Methylcellulose described in Japanese Pharmacopoeia, 17th edition.

The content of HPMC and/or MC in alcohol composition A is in the range between 0.1 parts by mass and 4.0 parts by mass. For example, the content is preferably in the range between 0.1 parts by mass and 3.8 parts by mass, more preferably 0.1 parts by mass and 3.5 parts by mass, and still more preferably 1.0 parts by mass and 3.0 parts by mass, in terms of the thickening property imparted to the alcohol composition.

[Features]

Alcohol composition A is not particularly limited in terms of other properties, so long as it contains the prescribed alcohol, water, and water-soluble cellulose ether in the above-mentioned amounts, and has a loss tangent (tan δ) of 0.10 to 1.00 when measured at 20° C. under the condition of being a frequency of 1 Hz and a strain of 0.1%.

The range of viscosity encompassed by alcohol composition A according to embodiments of the invention can provide various desirable characteristics. For example, in order to be prevented from dripping out and/or to have a good application feeling, the viscosity when measured with a viscometer at 20° C. is preferably in the range between 2,500 mPa·s and 30,000 mPa·s, more preferably 3,000 mPa·s and 28,000 mPa·s, and still more preferably 3,200 mP·s and 26,000 mPa·s. The viscosity of alcohol composition A is the value measured by the method as described in "Viscosity of alcohol composition" in Examples below.

While the loss tangent (tan δ) of alcohol composition A, when measured at 20° C. under the condition of being a frequency of 1 Hz and a strain of 0.1%, is in the range between 0.10 and 1.00, for example, the loss tangent of alcohol composition A is preferably in the range between 0.10 and 0.90, and more preferably between 0.15 and 0.85, in order to be prevented from dripping out and/or to have a good application feeling. The loss tangent (tan δ) of alcohol composition A is the value measured by the method as described in "Loss tangent" in Examples below.

The transmittance of alcohol composition A is not particularly limited, but in order to make a good appearance, is preferably 10.0 wt % or more, more preferably 14.0% or more, still more preferably 20.0% or more, and still even more preferably 24.0% or more. The upper limit of the transmittance of alcohol composition A is not particularly limited, but may be less than 65.0%, for example. The transmittance of alcohol composition A is the value measured according to the method as described in "Transmittance" in Examples below.

<Alcohol Composition B>

Alcohol composition B has a viscosity that is easy to apply and difficult to spill down, and also has a transmittance equal to or more than 65.0%, resulting in having high transparency and a moist application feeling. The dissolved state of HPMC and/or MC is sufficiently stable in alcohol composition B, and as a result, alcohol composition B can have a maintained viscosity stability, high transparency and an excellent appearance.

[Alcohol, Water, and Water-Soluble Cellulose Ether]

The same alcohol, water, and water-soluble cellulose ether in alcohol composition B can be used as in alcohol composition A.

The content of alcohol in alcohol composition B is in the range between 40.0 parts by mass and 88.0 parts by mass. For example, from the viewpoint of the transparency and disinfection effect of the alcohol composition, the content is preferably in the range between 45.0 parts by mass and 85 parts by mass, more preferably 50.0 parts by mass and 82.0 parts by mass, and still more preferably 60.0 parts by mass and 82.0 parts by mass.

The content of water in alcohol composition B is in the range between 8.0 parts by mass and 59.9 parts by mass. For example, from the viewpoint of the transparency of the alcohol composition, the content is preferably in the range between 11.0 parts by mass and 54.9 parts by mass, more preferably 14.0 parts by mass and 49.9 parts by mass, and still more preferably 14.0 parts by mass and 39.9 parts by mass.

The content of HPMC, MC or both in alcohol composition B is in the range between 0.1 parts by mass and 4 parts by mass. For example, the content is preferably in the range between 0.1 parts by mass and 3.8 parts by mass, more preferably 0.1 parts by mass and 3.5 parts by mass, and still more preferably 1.0 parts by mass and 3.0 parts by mass, in terms of the thickening effect and transparency imparted to the alcohol composition.

[Features]

Embodiments of Alcohol composition B may encompass a range of properties, so long as it contains the prescribed alcohol, water, and water-soluble cellulose ether in the above-mentioned amounts, and has a transmittance equal to or more than 65.0%.

The viscosity of alcohol composition B may vary within various ranges depending on the desired properties of the composition. For example, in order to have a moist application feeling, the viscosity when measured with a viscometer at 20° C. is preferably in the range between 1,500 mPa·s and 30,000 mPa·s, more preferably 2,500 mPa·s and 26,000 mPa·s, and still more preferably 3,000 mPa·s and 20,000 mPa·s. The viscosity of alcohol composition B is the value measured by the method as described in "Viscosity of alcohol composition" in Examples below.

The transmittance of alcohol composition B is equal to or more than 65.0%. For example, in order that alcohol composition B has a good appearance, the transmittance is preferably 70.0 wt % or more, more preferably 72.0% or more, still more preferably 75.0% or more, and still even more preferably 80.0% or more. The upper limit of the transmittance of alcohol composition B is not particularly limited, but may be 100.0%, for example. The transmittance of alcohol composition B is the value measured by the method as described in "Transmittance" in Examples below.

The loss tangent (tan δ) of alcohol composition B, when measured at 20° C. under the condition of being a frequency of 1 Hz and a strain of 0.1% according to some embodiments may be more than 1.00. The upper limit of the loss tangent (tan δ) of alcohol composition B when measured at 20° C. under the condition of being a frequency of 1 Hz and a strain of 0.1% is preferably 5.00, more preferably 3.50, and still more preferably 2.30, to provide an alcohol composition B which has a good application feeling, and even still more preferably 1.55, to provide an alcohol composition B can be prevented from dripping out. The loss tangent (tan δ) of alcohol composition B is the value measured by the method as described in "Loss tangent" in Examples below.

<Alcohol Composition C>

Even if the alcohol concentration is relatively high, alcohol composition C contains water-soluble cellulose ethers in the dissolved state such that its thickening property is exhibited. Furthermore, alcohol composition C is also characterized by having not only a technical feature of having a loss tangent (tan δ) of 0.10 to 1.00 when measured at 20° C. under the condition of being a frequency of 1 Hz and a strain of 0.1% but also a technical feature of having a transmittance equal to or more than 65.0%.

By having such technical features, alcohol composition C can be prevented from dripping out, can retain stable viscosity, can have an excellent appearance, as well as can have a good application feeling lacking stickiness, in addition to having a viscosity that is easy to apply and difficult to spill down, even with a high concentration of alcohol. As a result, alcohol composition C can even take, for example, a gel form with appropriate viscosity.

[Alcohol, Water, and Water-Soluble Cellulose Ether]

The same alcohol, water, and water-soluble cellulose ether in alcohol composition C can be used as in alcohol composition A.

The content of alcohol in alcohol composition C is in the range between 60.0 parts by mass and 88.0 parts by mass. For example, from the viewpoint of the thickening property and transparency of the alcohol composition, the content is preferably in the range between 60.0 parts by mass and 87.0 parts by mass, and more preferably 60.0 parts by mass and 85.0 parts by mass.

The content of water in alcohol composition C is in the range between 8.0 parts by mass and 39.9 parts by mass. For example, from the viewpoint of the thickening property and transparency imparted to the alcohol composition, the content is preferably in the range between 9.0 parts by mass and 39.9 parts by mass, and more preferably 11.0 parts by mass and 39.9 parts by mass.

The content of HPMC, MC or both in alcohol composition C is in the range between 0.1 parts by mass and 4.0 parts by mass. For example, the content is preferably in the range between 0.1 parts by mass and 3.8 parts by mass, more preferably 0.1 parts by mass and 3.5 parts by mass, and still more preferably 1.0 parts by mass and 3.0 parts by mass, in terms of the thickening property and transparency imparted to the alcohol composition.

[Features]

Alcohol composition C may be characterized by a range of other properties, so long as it contains the prescribed alcohol, water, and water-soluble cellulose ether in the above-mentioned amounts, and has a loss tangent (tan δ) of 0.10 to 1.00 when measured at 20° C. under the condition of being a frequency of 1 Hz and a strain of 0.1% and a transmittance equal to or more than 65.0%.

The viscosity of alcohol composition C may vary according to the desired features. For example, in order to be prevented from dripping out, and/or to have a good application feeling, the viscosity when measured with a viscometer at 20° C. is preferably in the range between 2,500 mPa·s and 30,000 mPa·s, more preferably 3,000 mPa·s and 28,000 mPa·s, still more preferably 4,000 mP·s and 26,000 mPa·s, and even still more preferably 4,500 mP·s and 26,000 mPa·s. The viscosity of alcohol composition C is the value measured by the method as described in "Viscosity of alcohol composition" in Examples below.

The transmittance of alcohol composition C is equal to or more than 65.0%. For example, in order that alcohol composition C has an excellent appearance, the transmittance is preferably 70.0% or more, more preferably 72.0% or more, and still more preferably 76.0% or more. The upper limit of the transmittance of alcohol composition C is not particularly limited, but may be 100.0%, for example. The transmittance of alcohol composition C is the value measured by the method as described in "Transmittance" in Examples below.

While the loss tangent (tan δ) of alcohol composition C, when measured at 20° C. under the condition of being a frequency of 1 Hz and a strain of 0.1%, is in the range between 0.10 and 1.00, for example, the loss tangent of alcohol composition C is preferably in the range between 0.10 and 0.90, and more preferably between 0.15 and 0.85, in order to be prevented from dripping out, and/or to have a good application feeling. The loss tangent (tan δ) of alcohol composition C is the value measured by the method as described in "Loss tangent" in Examples below.

<Additives>

The alcohol composition according to one embodiment of the present invention may contain other additives in addition to alcohol, water, and water-soluble cellulose ether in order to impart the desired properties to the alcohol composition.

Additives are not particularly limited so long as they do not prevent the present invention from solving the problems, but may include, for example, disinfectants, viscosity modifying agents, pH adjusting agents, fragrances, pigments, dyes, antioxidants, preservative agents and moisturizers.

Examples of disinfectants include benzalkonium chloride, triclosan, and hinokitiol.

Examples of viscosity modifying agents include water-soluble polymers such as guar gum, locust bean gum, carboxymethyl cellulose, hydroxyethyl cellulose, hydrophobized hydroxypropyl methyl cellulose, cationized hydroxyethyl cellulose, carboxyvinyl polymer, and polyvinyl alcohol. In addition, hydroxyethyl cellulose is preferably excluded. This is because the lower degree of molar substitution in hydroxyethyl cellulose causes the compatibility to become deteriorated, while the higher degree of molar substitution in hydroxyethyl cellulose causes the flowability to become high, thereby degrading the liquid dripping and application feeling. From the viewpoint of the application feeling and the reduction of synthetic polymer used, carboxyvinyl polymer is preferably excluded. Therefore, it is preferable that alcohol composition A, alcohol composition B and alcohol composition C do not contain both of hydroxyethyl cellulose and carboxyvinyl polymer.

Examples of pH adjusting agents include alkaline metal hydroxides such as sodium hydroxide and potassium hydroxide; alkaline earth metal hydroxides such as calcium hydroxide and magnesium hydroxide; ammonium carbonate, ammonia, ammonia water, trisodium phosphate, disodium hydrogen phosphate, dipotassium hydrogen phosphate; secondary alkylamines such as dimethylamine and diethylamine; tertiary alkylamines such as trimethylamine and triethylamine; monoethanolamine, isopropanolamine, diethanolamine, diisopropanolamine, triethanolamine, triisopropanolamine and polyethanolamine.

Examples of fragrances include rose oil, jasmine oil, lavender oil, ylang-ylang oil, peppermint oil, geranium oil, patchouli oil, sandalwood oil, cinnamon oil, lemon oil, orange oil, bergamot oil, limonene, β-caryophyllene, cis-3-hexenol, linalool, farnesol, β-phenylethyl alcohol, 2,6-nonadienal, citral, α-hexyl cinnamaldehyde, iota-carvone, cyclopentadecanone, linalyl acetate, γ-undecalactone and aurantiol.

Examples of pigments include titanium dioxide, zinc oxide, barium sulfate, zinc oxide coated or compounded with silicic anhydride, iron oxide (bengara), iron titanate, γ-iron oxide, iron yellow oxide, ochre, black iron oxide, carbon black, and low-order titanium dioxide.

Examples of dyes include acid dyes, nitro dyes, disperse dyes, basic dyes, and oxidative dye intermediates.

Examples of antioxidants include tocopherol, tocopherol acetate, ascorbic acid, butyl hydroxyanisole, and dibutyl hydroxytoluene.

Examples of preservative agents include methylparaben, ethylparaben, propylparaben, butylparaben, and phenoxyethanol.

Examples of moisturizers include hyaluronic acid, sodium hyaluronate, polyethylene glycol, mucopolysaccharide, urea, sorbitol, chondroitin sulfate, pyrrolidone carboxylic acid, sodium lactate, polyaspartic acid, glycerin, propylene glycol, 1,3-propanediol, dipropylene glycol, 1,3-butanediol, diglycerin, and pentylene glycol.

Additives may be used either individually or in combination of two or more of the above-mentioned additives. Additives may be commercially available or may be manufactured by known methods.

The content of additives may vary according to the desired properties and applications to be given to the alcohol composition, but for example, from the viewpoint of the storage stability of the alcohol composition, the content is preferably in the range between 0.001 parts by mass and 20.0 parts by mass. In addition, when additives are selected from the group consisting of glycerin, propylene glycol, 1,3-propanediol, dipropylene glycol, 1,3-butanediol, diglycerin and pentylene glycol, the content of additives is preferably in the range between 0.001 part by mass and 10 parts by mass in terms of solubility.

<Method of Producing Alcohol Composition>

So long as the alcohol composition according to one embodiment of the present invention can be obtained, the production method is not particularly limited. In addition, water-soluble cellulose ethers such as HPMC and MC are poorly soluble in alcohols. As such, when the alcohol concentration is high, it can be difficult to sufficiently hydrate and dissolve water-soluble cellulose ethers. As a result, only the surface of water-soluble cellulose ethers becomes wet, thereby causing partial dissolution and/or formation of agglomerates (mamako), leading to sedimentation and precipitation of water-soluble cellulose ethers following the preparation of the alcohol composition. These problems may result in an alcohol composition lacking desired properties due to insufficient viscosity and poor transparency.

In view of these problems, the present inventors intensively engaged in research through a trial-and-error process for various processes to find a method capable of suppressing not only the occurrence of mamako during the dissolution of water-soluble cellulose ethers but also the sedimentation and precipitation of water-soluble cellulose ethers after the preparation of the alcohol composition, even with a high alcohol concentration. However, surprisingly, the following steps were carried out in sequence in a step-by-step manner: dispersing water-soluble cellulose ethers such as HPMC and MC in a first alcohol to obtain a dispersion solution; mixing the dispersion solution with water to obtain a dissolved solution of water-soluble cellulose ethers; and mixing the dissolved solution with a second alcohol to obtain an alcohol composition, whereby suppressing the occurrence of mamako during the dissolution of water-soluble cellulose ethers, and the sedimentation and precipitation of water-soluble cellulose ethers after the preparation of the alcohol composition. In this way, the present inventors succeeded in producing all of alcohol composition A, alcohol composition B, and alcohol composition C. Therefore, it is preferable that the alcohol composition according to one embodiment of the present invention is produced by a method that includes the above steps. A preferred method of producing the alcohol composition according to one embodiment of the present invention is described below.

The preferred method of producing the alcohol composition according to one embodiment of the present invention includes a step of dispersing at least one water-soluble cellulose ether selected from the group consisting of HPMC and MC in a first alcohol to obtain a dispersion solution (hereinafter also referred to as a "step of obtaining dispersion solution"); a step of mixing the dispersion solution with water followed by dissolving the water-soluble cellulose ether to obtain a dissolved solution of water-soluble cellulose ether (hereinafter also referred to as a "step of obtaining dissolved solution"); and a step of mixing the dissolved solution with a second alcohol to obtain an alcohol composition (hereinafter also referred to as a "step of obtaining alcohol composition").

[Step of Obtaining Dispersion Solution]

In the step of obtaining dispersion solution, the cellulose ether of HPMC, MC or both is dispersed in a first alcohol to obtain a dispersion solution.

This method is characterized in that alcohols are blended in two stages: a first in a first stage, and second alcohol in a second stage. In addition, in this method, the content of the first alcohol is preferably an amount that does not interfere with sufficient hydration of the water-soluble cellulose ether. For example, a constant relationship between the mass of the first alcohol and the total mass of the first and second alcohols improves the dissolution stability of water-soluble cellulose ether, and allows the water-soluble cellulose ether to be hydrated very well. In order to achieve sufficient hydration of the water-soluble cellulose ether, the ratio of the mass of the first alcohol relative to the total mass of the first and second alcohols ([first alcohol]/[first alcohol+second alcohol]); hereinafter also referred to as the "first alcohol content ratio") is preferably equal to or less than 0.70, and more preferably equal to or less than 0.61. If the ratio is more than 0.70, the water ratio in the dissolved solution becomes small in the subsequent step of obtaining dissolved solution so that the amount of water that can contribute to dissolution of the water-soluble cellulose ether may be insufficient. The resulting insufficient hydration may give rise to insufficient dissolution of the water-soluble cellulose ether, and the obtained alcohol composition may not exhibit the expected thickening property.

For example, if the mass of the first alcohol is 20 parts by mass and the first alcohol content ratio is 0.267, the total mass of the alcohols is 75 parts by mass, and the mass of the second alcohol is 55 parts by mass.

This method includes dividing the alcohol into two parts, the first alcohol and the second alcohol, and dispersing the water-soluble cellulose ether in the first alcohol. This removes the need for the use of hot water normally required in the preliminarily preparation of an aqueous solution of water-soluble cellulose ether. As a result, there is no need to carry out cooling treatment, that is, cooling the solution so as to be at a temperature equal to or less than the dissolution temperature after heating, translating to reduced manufacturing time and power costs.

The conditions for dispersing the water-soluble cellulose ether in the first alcohol are not particularly limited. Examples of the conditions include conditions for dispersing a solid in a solvent as known in the art. For example, the dispersion solution can be obtained by contacting the first alcohol with the water-soluble cellulose ether followed by subjecting the resultant to mixing treatment such as stirring treatment to disperse the water-soluble cellulose ether in the first alcohol.

When stirring treatment is employed as mixing treatment, the stirring means are not particularly limited. Examples of stirring means include stirring means using stirring devices such as homogenizer, homomixer, homodisper, flowjet mixer, ultramixer, colloid mill, and three-one motor.

The stirring temperature is not particularly limited, but preferably in the range between 0° C. and 40° C., and more preferably between 0° C. and 35° C.; the stirring time is not particularly limited, but preferably in the range between 1 minute and 30 minutes, and more preferably between 5 minutes and 15 minutes.

In the step of obtaining dispersion solution, it is possible to say that a uniform dispersion has been obtained by visually confirming that there are virtually no clumps of water-soluble cellulose ether (agglomerates (mamako)), or no other parts of water-soluble cellulose ether that are in the pre-mixed state without being dispersed or that are agglomerated. The dispersion solution preferably remains in a homogeneous state for at least one hour after being left to stand. The water-soluble cellulose ether is preferably in a powder form to be well dispersed in the first alcohol, more preferably in a powder form with the average particle size between 10 μm to 100 μm on a volume basis according to dry laser diffraction method.

[Step of Obtaining Dissolved Solution]

In the step of obtaining dissolved solution, the dispersion solution obtained in the step of obtaining dispersion solution is mixed with water to dissolve the water-soluble cellulose ether, resulting in a dissolved solution.

While the temperature of water may be set as appropriate depending on the type of water-soluble cellulose ether, examples of the temperature include in the range between 0° C. and 35° C. Taking into consideration that the lower temperature the water-soluble cellulose ether is at, the higher solubility the water-soluble cellulose ether has, the temperature is preferably in the range between 0° C. and 30° C., and more preferably between 0° C. and 20° C.

The conditions for mixing the dispersion solution with water to dissolve the water-soluble cellulose ether are not particularly limited. Examples of the conditions include conditions for dissolving a substance contained in a dispersion solution in water as known in the art. For example, from the viewpoint of workability, it is preferable to add water to the dispersion solution followed by subjecting the resultant to mixing treatment.

As mixing treatment, it is preferable to employ stirring treatment. The stirring means are not particularly limited. Examples of stirring means include stirring means using stirring devices such as homogenizer, homomixer, homodisper, flowjet mixer, ultramixer, colloid mill, and three-one motor. The stirring means may be the same stirring means employed in the step of obtaining dispersion solution, or may be the different stirring means.

The stirring temperature is not particularly limited, so long as the temperature allows the water-soluble cellulose ether to be dissolved. The temperature is preferably in the range between 0° C. and 35° C., and more preferably 0° C. and 25° C. The stirring time is not particularly limited, so long as the time is a time when the dissolution of water-soluble cellulose ether is completed. The time is preferably in the range between 10 minutes and 60 minutes.

In the step of obtaining dissolved solution, it is possible to say that the dissolved solution has been obtained by visually confirming that there is virtually no separation or precipitation of water-soluble cellulose ether. In the step of obtaining dissolved solution, part or all of the step may be carried out while cooling in order to improve the solubility of water-soluble cellulose ether.

[Step of Obtaining Alcohol Composition]

In the step of obtaining alcohol composition, the alcohol composition is obtained by mixing the dissolved solution obtained in the step of obtaining dissolved solution with the second alcohol.

The conditions for mixing the dissolved solution with the second alcohol to obtain an alcohol composition are not particularly limited. Examples of the conditions include conditions for mixing two types of liquids as known in the art. For example, from the viewpoint of workability, it is preferable to add the second alcohol to the dissolved solution followed by subjecting the resultant to stirring treatment or other mixing treatment. The stirring means are not particularly limited. Examples of stirring means include stirring means using stirring devices such as homogenizer, homomixer, homodisper, flowjet mixer, ultramixer, colloid mill, and three-one motor. The stirring means may be the same stirring means employed in the step of obtaining dispersion solution and/or the step of obtaining dissolved solution, or may be the different stirring means. In addition, in order to improve the solubility stability of water-soluble cellulose ether in the alcohol composition and the uniformity of each component in the alcohol composition, it is preferable to subject the dissolved solution and the second alcohol to strong mixing treatment, it is more preferable to subject the dissolved solution and the second alcohol to vigorous mixing treatment, and it is still more preferable to subject the dissolved solution and the second alcohol to homogenizing treatment.

The stirring temperature is not particularly limited, but is preferably in the range between 0° C. and 35° C., and more preferably 0° C. and 25° C. The stirring time is not particularly limited, but is preferably in the range between 20 minutes and 90 minutes.

In the step of obtaining alcohol composition, it is possible to say that the alcohol composition has been obtained by visually confirming that there is virtually no separation or precipitation of water-soluble cellulose ether. If the dissolution of water-soluble cellulose ether is insufficient, the separated or precipitated portion of water-soluble cellulose ether tends to settle out when the alcohol composition is allowed to stand for one week. Therefore, it is preferable that in the alcohol composition, no separated or precipitated water-soluble cellulose ether can be substantially observed when the composition is allowed to stand for one week. In the step of obtaining alcohol composition, part or all of the step may be carried out while cooling in order to improve the solubility of water-soluble cellulose ether.

<Methods of Producing Alcohol Compositions a to C>

Resulting from extensive studies, the present inventors have found out that alcohol composition A, alcohol composition B, or alcohol composition C can be optionally produced by setting the degree of substitutions of methoxy groups (DS) and the molar substitutions of hydroxypropoxy groups (MS) in the water-soluble cellulose ether, the alcohol concentration (% by mass; X), and the first alcohol content ratio (%; Y) so as to become in a certain relationship.

That is, with the use of the above-mentioned preferred method of producing the alcohol composition according to one embodiment of the present invention including the step of obtaining dispersion solution, the step of obtaining dissolved solution and the step of obtaining alcohol composition, alcohol composition A, alcohol composition B, and alcohol composition C can be produced if DS, MS, X, and Y, and Z which is calculated by the following formula using the values, are made to have the relationship described in Tables 1 to 3 below.

$$(DS+MS)/X \times Y = Z \text{ (wherein } X > Y\text{)}$$

In addition, since each value of DS, MS, X, Y, and Z in Tables 1 to 3 is a rough indication, it should not be interpreted to mean that each alcohol composition cannot be produced unless DS, MS, X, Y, and Z are within the range of the values indicated in Tables 1 to 3.

Alcohol composition A may be produced when DS, MS, X, Y, and Z meet the conditions shown in Table 1. In Table 1, the water-soluble cellulose ether employed in Condition I is MC, and the water-soluble cellulose ethers employed in Conditions I to IV are HPMC.

TABLE 1

| Conditions | DS | MS | X | Y | Z |
|---|---|---|---|---|---|
| I | 1.0~2.2 | 0.00 | 60.0~80.0 | 10~70 | 0.21~2.40 |
| II | 1.5~2.2 | 0.15~0.35 | 83.0~93.0 | 10~70 | 0.22~1.70 |
| III | 1.5~2.2 | 0.10~0.21 | 68.0~80.0 | 10~70 | 0.22~2.00 |
| IV | 1.0~1.8 | 0.10~0.30 | 60.0~80.0 | 10~70 | 0.20~2.00 |

The DS and MS in HPMC employed in Conditions I to IV are preferably in a certain relationship in terms of the solubility of HPMC in the alcohol composition and the thickening property imparted to the alcohol composition. For example, HPMC employed in Condition II preferably has a DS of 1.60 to 2.10 and an MS of 0.17 to 0.30; HPMC employed in Condition III preferably has a DS of 1.60 to 2.10 and an MS of 0.12 to 0.21; and HPMC employed in Condition IV preferably has a DS of 1.20 to 1.70 and an MS of 0.17 to 0.30.

In addition, taking into consideration that alcohol composition A having the excellent workability and the higher solubility of water-soluble cellulose ether can be obtained accordingly, it is preferable that Z in Condition I is in the range between 0.40 and 1.60; Z in Condition II is in the range between 0.42 and 1.70; Z in Condition III is in the range between 0.45 and 1.80; and Z in Condition IV is in the range between 0.38 and 1.80.

Alcohol composition B may be produced when DS, MS, X, Y, and Z meet the conditions shown in Table 2. In Table 2, the water-soluble cellulose ether employed in Condition I is MC, and the water-soluble cellulose ethers employed in Conditions I to IV are HPMC.

TABLE 2

| Conditions | DS | MS | X | Y | Z |
|---|---|---|---|---|---|
| I | 1.0~2.2 | 0.00 | 30.0~68.0 | 10~70 | 0.25~2.40 |
| II | 1.5~2.2 | 0.15~0.35 | 30.0~88.0 | 10~70 | 0.23~2.60 |
| III | 1.5~2.2 | 0.10~0.21 | 30.0~75.0 | 10~70 | 0.22~2.30 |
| IV | 1.0~1.8 | 0.10~0.30 | 30.0~70.0 | 10~70 | 0.21~2.10 |

The OS and MS in HPMC employed in Conditions II to IV are preferably in a certain relationship in terms of the solubility of HPMC in the alcohol composition and the thickening property imparted to the alcohol composition. For example, HPMC employed in Condition II preferably has a DS of 1.60 to 2.10 and an MS of 0.17 to 0.30; HPMC employed in Condition III preferably has a DS of 1.60 to 2.10 and an MS of 0.12 to 0.21; and HPMC employed in Condition IV preferably has a DS of 1.20 to 1.70 and an MS of 0.17 to 0.30.

In addition, taking into consideration that alcohol composition B having the excellent workability and the higher solubility of water-soluble cellulose ether can be obtained accordingly, it is preferable that Z in Condition I is in the range between 0.51 and 1.83; Z in Condition II is in the range between 0.42 and 2.30; Z in Condition III is in the range between 0.45 and 2.00; and Z in Condition IV is in the range between 0.45 and 1.80.

Alcohol composition C may be produced when OS, MS, X, Y, and Z meet the conditions shown in Table 3. In Table 3, the water-soluble cellulose ether employed in Condition I is MC, and the water-soluble cellulose ethers employed in Conditions II to IV are HPMC.

TABLE 3

| Conditions | DS | MS | X | Y | Z |
|---|---|---|---|---|---|
| I | 1.0~2.2 | 0.00 | 60.0~68.0 | 10~70 | 0.24~2.20 |
| II | 1.5~2.2 | 0.10~0.35 | 83.0~88.0 | 10~70 | 0.23~1.90 |
| III | 1.5~2.2 | 0.10~0.21 | 68.0~75.0 | 10~70 | 0.22~2.00 |
| IV | 1.0~1.8 | 0.10~0.30 | 60.0~70.0 | 10~70 | 0.21~2.00 |

The DS and MS in HPMC employed in Conditions I to IV are preferably in a certain relationship in terms of the solubility of HPMC in the alcohol composition and the thickening property imparted to the alcohol composition. For example, HPMC employed in Condition II preferably has a DS of 1.60 to 2.10 and an MS of 0.17 to 0.30; HPMC employed in Condition III preferably has a DS of 1.60 to 2.10 and an MS of 0.12 to 0.21; and HPMC employed in Condition IV preferably has a DS of 1.20 to 1.70 and an MS of 0.17 to 0.30.

In addition, taking into consideration that alcohol composition C having the excellent workability and the higher solubility of water-soluble cellulose ether can be obtained accordingly, it is preferable that Z in Condition I is in the range between 0.54 and 1.78; Z in Condition II is in the range between 0.47 and 1.82; Z in Condition III is in the range between 0.45 and 1.80; and Z in Condition IV is in the range between 0.45 and 1.80.

<Usage of Alcohol Composition>

The usage of the alcohol composition according to one embodiment of the present invention is not particularly limited. For example, since the alcohol composition can contain ethanol and/or isopropanol with a high concentration, the alcohol composition may be preferably used in disinfection applications, and more preferably in hand disinfection applications. Among the alcohol compositions, alcohol composition A and alcohol composition C have a loss tangent (tan δ) of 0.10 to 1.00 when measured at 20° C. under the condition of being a frequency of 1 Hz and a strain of 0.1%. This means that they have a moderate viscosity and can be in the form of gel. Thus, such gel disinfection alcohol composition can be used in a variety of settings in daily life and healthcare.

The invention further encompasses the following items:

1. An alcohol composition comprising 60.0 parts by mass to 93.0 parts by mass of at least one alcohol selected from the group consisting of ethanol and isopropanol, 3.0 parts by mass to 39.9 parts by mass of water, and 0.1 parts by mass to 4.0 parts by mass of at least one water-soluble cellulose ether selected from the group consisting of hydroxypropyl methylcellulose and methylcellulose, wherein the alcohol composition has a loss tangent (tan δ) of 0.10 to 1.00 when measured at 20° C. under the condition of being a frequency of 1 Hz and a strain of 0.1%.

2. The alcohol composition according to item 1, wherein the alcohol composition has a viscosity equal to or more than 2,500 mPa·s when measured with a viscometer at 20° C. using a 2.0% by mass aqueous solution.

3. An alcohol composition comprising 40.0 parts by mass to 88.0 parts by mass of at least one alcohol selected from the group consisting of ethanol and isopropanol, 8.0 parts by mass to 59.9 parts by mass of water, and 0.1 parts by mass to 4.0 parts by mass of at least one water-soluble cellulose ether selected from the group consisting of hydroxypropylmethylcellulose and methylcellulose, wherein the alcohol composition has a transmittance equal to or more than 65.0%.

4. The alcohol composition according to item 3, wherein the alcohol composition has a viscosity equal to or more than 1,500 mPa·s when measured with a viscometer at 20° C. using a 2.0% by mass aqueous solution.

5. An alcohol composition comprising 60.0 parts by mass to 88.0 parts by mass of at least one alcohol selected from the group consisting of ethanol and isopropanol, 8.0 parts by mass to 39.9 parts by mass of water, and 0.1 parts by mass to 4.0 parts by mass of at least one water-soluble cellulose ether selected from the group consisting of hydroxypropyl methylcellulose and methylcellulose, wherein the alcohol composition has a loss tangent (tan δ) of 0.10 to 1.00 when measured at 20° C. under the condition of being a frequency of 1 Hz and a strain of 0.1%, and has a transmittance equal to or more than 65.0%.

6. The alcohol composition according to item 5, wherein the alcohol composition has a viscosity equal to or more than 2,500 mPa·s when measured with a viscometer at 20° C. using a 2.0% by mass aqueous solution.

7. The alcohol composition according to any one of claims 1 to 6, wherein the alcohol composition does not comprise at least one additive selected from the group consisting of hydroxyethyl cellulose and carboxyvinyl polymer.

8. The alcohol composition according to any one of items 1 to 7, wherein the water-soluble cellulose ether is selected from the group consisting of hydroxypropyl methylcellulose having the degree of substitutions (DS) of methoxy groups in the range between 1.20 and 2.20 and the molar substitutions (MS) of hydroxypropoxy groups in the range between 0.10 and 0.60, and methylcellulose having the degree of substitutions (DS) of methoxy groups in the range between 1.20 and 2.20.
9. The alcohol composition according to any one of the claims 1 to 8, wherein the alcohol composition comprises more than 60.0 parts by mass of the at least one alcohol selected from the group consisting of ethanol and isopropanol.
10. The alcohol composition according to claim 9, wherein the composition comprises 1.0 parts by mass to 3.0 parts by mass of the water-soluble cellulose ether HPMC, and wherein the HPMC is characterized by the following parameters:
    a. the DS of methoxy groups in HPMC is 1.40, particularly from 1.45 to 2.0, more particularly from 1.48 to 1.87, still more particularly from 1.48 to 1.76;
    b. the MS of hydroxypropoxy groups in HPMC is 0.10, particularly from 0.10 to 0.30, more particularly from 0.15 to 0.25.
11. The alcohol composition according to claim 10, wherein the alcohol composition comprises 1.0% parts by mass to 3.0 parts by mass of the water-soluble cellulose ether MC, wherein the DS of the MC is from 1.5 to 2.0, particularly wherein the DS of the MC is from 1.79 to 1.81.

EXAMPLES

While the present invention will now be described in further detail with reference to examples and comparative examples, the present invention is not limited to what is described in these examples and comparative examples.
<Evaluation of Physical Properties>
[Viscosity of HPMC and MC]
With respect to each viscosity of HPMC and MC, the viscosity at 20° C. of 2.0% by mass aqueous solution of each water-soluble cellulose ether was determined by using a single cylindrical rotational viscometer according to the single rotational viscometer in the General Tests "Viscosity Determination" in The Japanese Pharmacopoeia, Seventeenth Edition.
[Viscosity of Alcohol Composition]
The viscosity of the alcohol composition was determined as the value when measured after 120 seconds at 30 rpm at 20° C. using a single cylinder viscometer ("DVM-BII" manufactured by Tokyo Keiki, rotor Nos. 2 to 4). If the viscosity is beyond 20,000 mPa·s, the viscosity was determined as the value when measured after 120 seconds at 20 rpm at 20° C. using a Brookfield type viscometer ("B8H" manufactured by Tokyo Keiki, rotor No. 5).
[Loss Tangent]
The loss tangent was measured for the alcohol composition using a rheometer ("MCR-301" manufactured by Anton Paar) in the following procedures.
The sample measurement section of the rheometer was pre-tempered to 25° C. The alcohol composition was poured into the CC27 measuring cup (a cylindrical aluminum container with a diameter of 30 mm and a height of 80 mm) up to the marked line (25 ml). The viscoelasticity of the alcohol composition poured into the measuring cup was measured by a bob cylinder (26.7 mm in diameter and 40.0 mm in height: CC27) at a frequency of 1 Hz when strain was applied in the range between 0.01% and 100.0%. The measurement section was kept constant at 25° C. The measured value of viscoelasticity was employed as the value of loss tangent.

[Transmittance]
The transmittance as a measure of transparency was measured at 720 nm for the alcohol composition at 20° C. using a photoelectric colorimeter ("PC-50" manufactured by KOTAKI) with a filter of 720 nm and a 20 mm cell.
[Liquid Dripping]
The alcohol composition was filled up in a dispenser container ("200 ml pump bottle", bore diameter: 3 mm, manufactured by FRCOLOR). Liquid dripping was evaluated by dispensing the alcohol composition as a gel three times consecutively from the dispenser container, and visually checking the liquid dripping, according to the following evaluation criteria.
<<Evaluation Criteria>>
    −: No liquid dripping was confirmed.
    +: The liquid dripping was confirmed one time out of three times.
    ++: The liquid dripping was confirmed two times out of three times.
    +++: The liquid dripping was confirmed all three times.
<Sensory Evaluation>
[Application Feeling]
The application feeling was confirmed by sensory evaluation directed to five panelists who excelled in evaluating the feeling for alcohol composition, according to the following method.
That is, the feeling for alcohol composition at the time when 5 ml of alcohol composition was placed on the back of hand of each panelist and applied to the entire hand was scored according to the following evaluation criteria-a. Then, the score with the highest number of respondents (the most frequent score) was adopted as the application feeling. In addition, since the composition with a loss tangent of more than 1.0 and a transmittance of 65.0% or more had no effect on application feeling, another evaluation criteria (evaluation criteria-b) was adopted.
<<Evaluation Criteria-a>>
    3: Good extensibility, no sticky feeling, and less dry feeling.
    2: Good extensibility, and moist application feeling.
    1: Sticky feeling.
    0: Poor extensibility, or difficulty in application due to spilling down from hands.
<<Evaluation Criteria-b>>
    2: Capable of applying due to no spilling down from hands, and less sticky feeling.
    1: Capable of applying due to no spilling down from hands.
    0: Difficult in applying due to spilling down from hands.
<Method of Producing Alcohol Composition>
[Materials Used]
For HPMC and MC, the samples listed in Table 4 (all manufactured by Shin-Etsu Chemical) were used. Ethanol (Fujifilm Wako Pure Chemical), isopropanol (Kishida), and glycerin (Kishida) were used as alcohols. Pure water was used for water.

TABLE 4

| Samples | Type | Degree of substitutions (DS) | Molar substitutions (MS) | Viscosity of 2% by mass aqueous solution (mPa·s) |
|---|---|---|---|---|
| CE-1 | MC | 1.79 | 0 | 4850 |
| CE-2 | MC | 1.81 | 0 | 8120 |
| CE-3 | HPMC | 1.87 | 0.24 | 4500 |
| CE-4 | HPMC | 1.87 | 0.25 | 10100 |
| CE-5 | HPMC | 1.75 | 0.16 | 4880 |

TABLE 4-continued

| Samples | Type | Degree of substitutions (DS) | Molar substitutions (MS) | Viscosity of 2% by mass aqueous solution (mPa · s) |
|---|---|---|---|---|
| CE-6 | HPMC | 1.75 | 0.15 | 13700 |
| CE-7 | HPMC | 1.76 | 0.16 | 58600 |
| CE-8 | HPMC | 1.46 | 0.25 | 4950 |
| CE-9 | HPMC | 1.43 | 0.2 | 13100 |
| CE-10 | HPMC | 1.48 | 0.25 | 85000 |
| CE-11 | HPMC | 1.76 | 0.15 | 1490 |

Example 1

Ethanol (20.0 g) accurately weighed as a first alcohol and CE-1 (2.0 g) were added to a 200 ml beaker, and the mixture was stirred for 2 min using a magnetic stirrer ("HS-360" manufactured by As One, 200 rpm to 300 rpm) to prepare a uniform dispersion solution. Then, while stirring, pure water (28.0 g) at 20° C. was added to the resulting dispersion solution to dissolve MC, and obtain a dissolved solution. Ethanol (50.0 g) as a second alcohol was added to the resulting dissolved solution, and the mixture was subjected to homogenization treatment for 4 minutes using a small homogenizer ("AHG-160D" manufactured by As One, 5,000 rpm) to produce the alcohol composition of Example 1.

Examples 2 to 36

The alcohol compositions of Examples 2 to 24, and 26 to 36 were produced in the same manner as in Example 1, except that the types and amounts of alcohols and samples shown in Table 5 were used.

Example 37

Ethanol (20.0 g) accurately weighed and hydroxypropyl methylcellulose (2.0 g) were added to a 200 ml beaker, and the mixture was stirred for 2 min using a magnetic stirrer ("HS-360" manufactured by As One, 200 rpm to 300 rpm) to prepare a uniform dispersion solution. Then, while stirring, pure water (26.0 g) at 20° C. was added to the resulting dispersion solution to dissolve HPMC, and obtain a dissolved solution. Ethanol (50.0 g) and glycerin (2.0 g) were added to the resulting dissolved solution, and the mixture was subjected to homogenization treatment for 4 minutes using a small homogenizer ("AHG-160D" manufactured by As One, 5,000 rpm) to produce the alcohol composition of Example 37.

Reference Example 1

Carboxyvinyl polymer (2.0 g) was added to pure water (98.0 g) and dissolved using a homomixer ("HM-310" manufactured by As One) to prepare a 2% by mass aqueous solution of carboxyvinyl polymer (carbomer).
Ethanol (70.0 g), pure water (9.98 g) at 20° C. and the 2% by mass aqueous solution of carbomer (20.0 g) were added to the resulting dissolved solution, and the mixture was subjected to homogenization treatment for 4 minutes using a small homogenizer ("AHG-160D" manufactured by As One, 5,000 rpm). The alcohol composition was produced by adding triethanolamine (0.02 g) to the resulting treated mixture and adjusting the pH to the range between 6 and 8.

<Evaluation Results>

Table 5 and Table 6 show the results of evaluating the viscosity, loss tangent, transmittance, liquid dripping, and application feeling of the alcohol compositions of Examples 1 to 37.

[Evaluation Results of Alcohol Composition A]

Even with high alcohol concentrations of 60% or more, alcohol compositions with a viscosity suitable for filling into containers and applying to the skin were obtained.

The alcohol compositions of Examples 1 to 11, 13, 15, 21 to 24, 26 to 29, and 34 to 36 had a loss tangent equal to or less than 1.00, thereby leading to the contribution of elasticity exceeding that of viscosity and retaining an excellent gel morphology. As a result, the alcohol compositions were not dripped out from the container, and could be applied on the entire hand without spilling down when placed on the hand. Most of the alcohol compositions with a loss tangent of 1.00 or less had good extensibility, were easy to spread, and had a good feeling with little stickiness.

[Evaluation Results of Alcohol Composition B]

Even with high alcohol concentrations of 60% or more, alcohol compositions with high transparency were obtained.

The alcohol compositions of Examples 4, 5, 8, 12 to 25, 27, 28, 30 to 34, 36, and 37 were highly transparent and had good appearance. With respect to the alcohol compositions, the liquid dripping from the container was a little confirmed but the extent was within usable range. The alcohol compositions with a loss tangent beyond 1.00 had a weak gel feeling and a smooth liquid form, and had a moist application feeling when applied on the hand.

[Evaluation Results of Alcohol Composition C]

Even with high alcohol concentrations of 60% or more, alcohol compositions with high transparency and a viscosity suitable for filling into containers and applying to the skin were obtained.

The alcohol compositions of Examples 4, 5, 8, 13, 15, 21 to 24, 27, 28, 34, and 36 were highly transparent and had good appearance. The alcohol compositions had a loss tangent equal to or less than 1.00, thereby leading to the contribution of elasticity exceeding that of viscosity and retaining an excellent gel morphology. As a result, the alcohol compositions were not dripped out from the container, and could be applied on the entire hand without spilling down when placed on the hand. Most of the alcohol compositions with a loss tangent of 1.00 or less had good extensibility, were easy to spread, and had a good feeling with little stickiness.

The alcohol composition of Example 25 was highly transparent and had good appearance. The alcohol composition had a loss tangent of more than 1.00, but was not dripped out from the container and could be applied on the entire hand without spilling down when placed on the hand. The alcohol composition had good extensibility, were easy to spread, and had not only a moisture feeling but also a good application feeling with little stickiness.

Furthermore, alcohol composition A, alcohol composition B, and alcohol composition C all contained the water-soluble cellulose ether at the sufficiently dissolved state, and thus had almost the same viscosity as immediately after preparation even after left to stand at room temperature for one week. On the other hand, the alcohol composition of Reference Example 1 containing as a thickening agent carbomer, which is readily soluble in ethanol, also had almost the same viscosity as immediately after preparation even after left to stand at room temperature for one week. These results show that the water-soluble cellulose ethers were almost insoluble in alcohols, but contained in alcohol composition A, alcohol composition B, and alcohol composition C at the well-dissolved state.

TABLE 5

| Examples | Alcohol(s) | Sample | Type | Content of sample (parts by mass) | Viscosity (mPa·s) | Content of alcohol (% by mass) [A] | Content of first alcohol (% by mass) [B] | First alcohol content ratio (%) [B]/[A] | Additives | Loss tangent | Transmittance (%) | Z |
|---|---|---|---|---|---|---|---|---|---|---|---|---|
| 1 | Ethanol | CE-1 | MC | 2.0 | 15,160 | 70.0 | 20.0 | 28.6 | | 0.43 | 46.4 | 0.73 |
| 2 | Ethanol | CE-1 | MC | 2.0 | 3,010 | 80.0 | 20.0 | 25.0 | | 0.22 | 14.7 | 0.56 |
| 3 | Ethanol | CE-2 | MC | 1.5 | 2,510 | 70.0 | 30.0 | 42.9 | | 1.00 | 48.2 | 1.01 |
| 4 | Ethanol | CE-8 | HPMC | 2.0 | 8,020 | 60.0 | 20.0 | 33.3 | | 0.87 | 77.4 | 0.95 |
| 5 | Ethanol | CE-9 | HPMC | 1.5 | 6,400 | 60.0 | 20.0 | 33.3 | | 0.87 | 78.0 | 0.91 |
| 6 | Ethanol | CE-10 | HPMC | 1.0 | 3,260 | 70.0 | 40.0 | 57.1 | | 0.77 | 55.4 | 1.41 |
| 7 | Ethanol | CE-8 | HPMC | 2.0 | 4,780 | 80.0 | 20.0 | 25.0 | | 0.19 | 14.1 | 0.53 |
| 8 | Ethanol | CE-7 | HPMC | 1.0 | 5,210 | 75.0 | 20.0 | 26.7 | | 0.79 | 86.5 | 0.68 |
| 9 | Ethanol | CE-6 | HPMC | 1.5 | 3,930 | 80.0 | 40.0 | 50.0 | | 0.56 | 37.6 | 1.19 |
| 10 | Ethanol | CE-5 | HPMC | 2.0 | 13,480 | 80.0 | 20.0 | 25.0 | | 0.56 | 24.1 | 0.82 |
| 11 | Ethanol | CE-5 | HPMC | 2.0 | 7,570 | 90.0 | 20.0 | 22.2 | | 0.39 | 33.6 | 0.52 |
| 12 | Ethanol | CE-1 | MC | 2.0 | 10,680 | 60.0 | 20.0 | 33.3 | | 1.21 | 70.1 | 0.99 |
| 13 | Ethanol | CE-1 | MC | 2.0 | 12,370 | 60.0 | 30.0 | 50.0 | | 0.95 | 67.6 | 1.49 |
| 14 | Ethanol | CE-4 | HPMC | 1.5 | 3,363 | 60.0 | 20.0 | 33.3 | | 1.89 | 99.0 | 1.18 |
| 15 | Ethanol | CE-4 | HPMC | 2.0 | 9,350 | 85.0 | 20.0 | 23.5 | | 0.88 | 82.5 | 0.59 |
| 16 | Ethanol | CE-4 | HPMC | 1.5 | 3,170 | 85.0 | 40.0 | 47.1 | | 1.90 | 78.8 | 1.17 |
| 17 | Ethanol | CE-3 | HPMC | 2.0 | 4,050 | 70.0 | 20.0 | 28.6 | | 2.25 | 98.7 | 0.86 |
| 18 | Ethanol | CE-3 | HPMC | 2.0 | 4,710 | 80.0 | 20.4 | 25.5 | | 1.81 | 91.2 | 0.66 |
| 19 | Ethanol | CE-6 | HPMC | 1.5 | 7,680 | 60.0 | 20.0 | 33.3 | | 1.37 | 98.3 | 1.08 |
| 20 | Ethanol | CE-10 | HPMC | 1.0 | 4,120 | 60.0 | 35.0 | 58.3 | | 3.40 | 78.6 | 1.68 |
| 21 | Ethanol | CE-10 | HPMC | 1.0 | 4,520 | 70.0 | 20.0 | 28.6 | | 0.66 | 70.9 | 0.71 |
| 22 | Ethanol | CE-6 | HPMC | 1.5 | 9,350 | 70.0 | 20.0 | 28.6 | | 0.99 | 96.2 | 0.78 |
| 23 | Ethanol | CE-6 | HPMC | 1.5 | 13,400 | 75.0 | 20.0 | 26.7 | | 0.61 | 85.2 | 0.68 |
| 24 | Ethanol | CE-7 | HPMC | 1.0 | 2,740 | 75.0 | 40.0 | 53.3 | | 0.89 | 71.8 | 1.37 |
| 25 | Isopropanol | CE-1 | MC | 1.5 | 2,661 | 60.0 | 20.0 | 33.3 | | 1.63 | 74.5 | 0.99 |
| 26 | Isopropanol | CE-2 | MC | 1.5 | 5,330 | 65.0 | 20.0 | 30.8 | | 0.79 | 63.6 | 0.86 |
| 27 | Isopropanol | CE-8 | HPMC | 2.0 | 23,000 | 60.0 | 20.0 | 33.3 | | 0.55 | 76.2 | 0.95 |
| 28 | Isopropanol | CE-7 | HPMC | 1.0 | 6,980 | 70.0 | 20.0 | 28.6 | | 0.68 | 95.5 | 0.78 |
| 29 | Isopropanol | CE-3 | HPMC | 2.0 | 13,710 | 85.0 | 20.0 | 23.5 | | 0.72 | 63.2 | 0.58 |
| 30 | Isopropanol | CE-3 | HPMC | 2.0 | 6,350 | 80.0 | 20.0 | 25.0 | | 1.55 | 88.9 | 0.66 |
| 31 | Isopropanol | CE-7 | HPMC | 1.5 | 3,746 | 75.0 | 42.9 | 57.1 | | 1.24 | 86.2 | 1.57 |
| 32 | Isopropanol | CE-5 | HPMC | 2.0 | 5,460 | 60.0 | 20.0 | 33.3 | | 1.78 | 99.5 | 1.17 |
| 33 | Isopropanol | CE-2 | MC | 1.5 | 3,930 | 50.0 | 30.0 | 60.0 | | 1.65 | 82.3 | 2.17 |
| 34 | Isopropanol | CE-5 | HPMC | 2.0 | 15,360 | 70.0 | 20.0 | 28.6 | | 0.36 | 85.7 | 0.78 |
| 35 | Ethanol | CE-11 | HPMC | 3.0 | 22,500 | 80.0 | 20.0 | 25.0 | | 0.49 | 31.0 | 0.48 |
| 36 | Ethanol | CE-11 | HPMC | 3.0 | 25,250 | 75.0 | 20.0 | 26.7 | | 0.42 | 74.5 | 0.55 |
| 37 | Ethanol/glycerin | CE-5 | HPMC | 2.0 | 10,070 | Ethanol 70.0 | 20.6 | 28.6 | Glycerin | 1.26 | 86.5 | 0.55 |

| Reference Example | Alcohol | Type | Content of sample (parts by mass) | Viscosity (mPa·s) | Content of alcohol (% by mass) [A] | Content of first alcohol (% by mass) [B] | First alcohol content ratio (%) [B]/[A] | Additives | Loss tangent | Transmittance (%) | Z |
|---|---|---|---|---|---|---|---|---|---|---|---|
| 1 | Ethanol | Carbomer | 0.4 | 6,110 | 70.0 | 70.0 | 100.0 | TEA | 0.10 | 95.9 | . |

TABLE 6

| Examples | Liquid dripping | Application feeling Evaluation criteria-a | Application feeling Evaluation criteria-b |
|---|---|---|---|
| 1 | − | 3 | |
| 2 | − | 3 | |
| 3 | − | 2 | |
| 4 | − | 2 | |
| 5 | − | 2 | |
| 6 | − | 3 | |
| 7 | − | 3 | |
| 8 | − | 3 | |
| 9 | − | 3 | |
| 10 | − | 3 | |
| 11 | − | 3 | |
| 12 | + | | 2 |
| 13 | − | 2 | |
| 14 | + | | 1 |
| 15 | − | 2 | |
| 16 | + | | 1 |
| 17 | ++ | | 1 |
| 18 | + | | 1 |
| 19 | + | | 2 |
| 20 | ++ | | 1 |
| 21 | − | 3 | |
| 22 | − | 2 | |
| 23 | − | 3 | |
| 24 | − | 2 | |
| 25 | + | | 1 |
| 26 | − | 3 | |
| 27 | − | 3 | |
| 28 | − | 3 | |
| 29 | − | 3 | |
| 30 | + | | 2 |
| 31 | + | | 2 |
| 32 | + | | 1 |
| 33 | + | | 1 |
| 34 | − | 3 | |
| 35 | − | 3 | |
| 36 | − | 3 | |
| 37 | + | | 2 |

We claim:

1. An alcohol composition consisting essentially of 60.0 parts by mass to 93.0 parts by mass of at least one alcohol selected from the group consisting of ethanol and isopropanol, 3.0 parts by mass to 39.9 parts by mass of water, and 0.1 parts by mass to 4.0 parts by mass of at least one water-soluble cellulose ether selected from the group consisting of hydroxypropyl methylcellulose (HPMC) and methylcellulose (MC),
   wherein the alcohol composition has a viscoelasticity loss tangent (tan δ) in the range of 0.10 to 1.00 when measured at 20° C. under the condition of being a frequency of 1 Hz and a strain of 0.1%,
   wherein the alcohol composition does not comprise at least one additive selected from the group consisting of hydroxyethyl cellulose and carboxyvinyl polymer, and
   wherein the water-soluble cellulose ether is characterized by the following parameters:
   a. the degree of substitution (DS) of methoxy groups in HPMC is ≥1.00;
   b. the molar substitution (MS) of hydroxypropoxy groups in HPMC is ≥0.10; or
   c. the DS of methoxy groups in MC is from 1.00 to 2.20.

2. The alcohol composition according to claim 1, wherein the alcohol composition has a viscosity equal to or more than 2,500 mPa·s when measured with a viscometer at 20° C. using a 2.0% by mass aqueous solution.

3. An alcohol composition consisting essentially of 40.0 parts by mass to 88.0 parts by mass of at least one alcohol selected from the group consisting of ethanol and isopropanol, 8.0 parts by mass to 59.9 parts by mass of water, and 0.1 parts by mass to 4.0 parts by mass of at least one water-soluble cellulose ether selected from the group consisting of HPMC and MC, wherein the alcohol composition has a transmittance at 720 nm equal to or more than 65.0%,
   wherein the alcohol composition does not comprise at least one additive selected from the group consisting of hydroxyethyl cellulose and carboxyvinyl polymer, and
   wherein the water-soluble cellulose ether is characterized by the following parameters:
   a. the degree of substitution (DS) of methoxy groups in HPMC is ≥1.00;
   b. the molar substitution (MS) of hydroxypropoxy groups in HPMC is ≥0.10; or
   c. the DS of methoxy groups in MC is from 1.00 to 2.20.

4. The alcohol composition according to claim 3, wherein the alcohol composition has a viscosity equal to or more than 1,500 mPa·s when measured with a viscometer at 20° C. using a 2.0% by mass aqueous solution.

5. An alcohol composition consisting essentially of 60.0 parts by mass to 88.0 parts by mass of at least one alcohol selected from the group consisting of ethanol and isopropanol, 8.0 parts by mass to 39.9 parts by mass of water, and 0.1 parts by mass to 4.0 parts by mass of at least one water-soluble cellulose ether selected from the group consisting of hydroxypropyl methylcellulose and methylcellulose, wherein the alcohol composition has a loss tangent (tan δ) of 0.10 to 1.00 when measured at 20° C. under the condition of being a frequency of 1 Hz and a strain of 0.1%, and has a transmittancy equal to or more than 65.0%,
   wherein the alcohol composition does not comprise at least one additive selected from the group consisting of hydroxyethyl cellulose and carboxyvinyl polymer, and
   wherein the water-soluble cellulose ether is characterized by the following parameters:
   a. the degree of substitution (DS) of methoxy groups in HPMC is ≥1.00;
   b. the molar substitution (MS) of hydroxypropoxy groups in HPMC is ≥0.10; or
   c. the DS of methoxy groups in MC is from 1.00 to 2.20.

6. The alcohol composition according to claim 5, wherein the alcohol composition has a viscosity equal to or more than 2,500 mPa·s when measured with a viscometer at 20° C. using a 2.0% by mass aqueous solution.

* * * * *